(12) United States Patent
Paterson

(10) Patent No.: US 8,310,249 B2
(45) Date of Patent: Nov. 13, 2012

(54) SURFACE GAP SOOT SENSOR FOR EXHAUST

(75) Inventor: Clark Paterson, Loveland, CO (US)

(73) Assignee: Woodward, Inc., Fort Collins, CO (US)

( * ) Notice: Subject to any disclaimer, the term of this patent is extended or adjusted under 35 U.S.C. 154(b) by 435 days.

(21) Appl. No.: 12/561,666

(22) Filed: Sep. 17, 2009

(65) Prior Publication Data

US 2011/0062973 A1    Mar. 17, 2011

(51) Int. Cl.
*G01R 27/08* (2006.01)
(52) U.S. Cl. ............ 324/693; 701/108; 73/114.71; 431/7; 60/286
(58) Field of Classification Search ............ 324/693; 60/285, 297, 295, 272, 286; 701/34, 108; 73/28.01, 116, 118.1; 205/775; 431/7
See application file for complete search history.

(56) References Cited

U.S. PATENT DOCUMENTS

| | | |
|---|---|---|
| 4,571,938 A | 2/1986 | Sakurai |
| 4,870,319 A | 9/1989 | Benedikt et al. |
| 5,253,475 A | 10/1993 | Kabasin |
| 5,777,216 A | 7/1998 | Van Duyne et al. |
| 6,192,740 B1 | 2/2001 | Thomas et al. |
| 6,735,941 B2 | 5/2004 | Saito et al. |
| 6,918,755 B1 | 7/2005 | Johnson et al. |
| 6,941,750 B2 | 9/2005 | Boretto et al. |
| 6,971,258 B2 | 12/2005 | Rhodes et al. |

(Continued)

FOREIGN PATENT DOCUMENTS

JP    59060018 A  *  4/1984

(Continued)

OTHER PUBLICATIONS

David P. Gardiner et al., Evaluation of a Spark Discharge Particulate Matter Sensor in a Turbocharged Diesel Engine, paper, Oct. 14-17, 2007, 9 pages, pp. 1-9, ICEF2007-1739, Charleston, South Carolina, USA.

(Continued)

*Primary Examiner* — Huy Q Phan
*Assistant Examiner* — Temilade S Rhodes-Vivour
(74) *Attorney, Agent, or Firm* — Reinhart Boerner Van Deuren P.C.

(57) ABSTRACT

A method and apparatus for sensing particulates within an exhaust flow are provided. The methods and apparatus utilize a soot sensor that includes opposed electrodes separated by an insulator. Preferably, a gap is formed between the electrodes and the insulator to prevent electrical current from flowing therebetween. The soot sensor, when positioned in an exhaust flow, will accumulate a layer of particulates on an outer surface thereof. As the layer of particulates increases the particulates will bridge the two electrodes permitting current flow. The sensor is configured with a proper geometry and potential difference between the electrodes to generate currents in the milli-amp range. Further, the sensor is configured to have a regenerative effect that causes the bridge to be broken when particles sees to impinge the soot sensor.

21 Claims, 6 Drawing Sheets

U.S. PATENT DOCUMENTS

| | | |
|---|---|---|
| 7,032,376 B1 | 4/2006 | Webb et al. |
| 7,278,304 B2 | 10/2007 | Zanini-Fisher et al. |
| 2005/0145023 A1 | 7/2005 | Rhodes et al. |
| 2005/0178675 A1 | 8/2005 | Hall |
| 2006/0021331 A1 | 2/2006 | Cizeron et al. |
| 2006/0287802 A1 | 12/2006 | Venghaus et al. |
| 2007/0056263 A1 | 3/2007 | Roach et al. |
| 2008/0028752 A1 | 2/2008 | Lee |
| 2008/0105567 A1* | 5/2008 | Okayama et al. .............. 205/775 |
| 2008/0282682 A1* | 11/2008 | C. et al. ............................ 60/291 |
| 2009/0241520 A1 | 10/2009 | Gendron et al. |
| 2009/0309571 A1* | 12/2009 | Katsuyama et al. ......... 324/71.1 |
| 2010/0049462 A1* | 2/2010 | Krafthefer et al. ............ 702/104 |

FOREIGN PATENT DOCUMENTS

| | | | |
|---|---|---|---|
| JP | 2001/033412 A | | 2/2001 |
| JP | 2006026483 A | * | 2/2006 |
| JP | 2006/266961 A | | 10/2006 |
| JP | 2009/512814 A | | 3/2009 |
| WO | WO 2008/027145 | | 3/2008 |
| WO | WO 2008/134060 A1 | | 11/2008 |

OTHER PUBLICATIONS

Woodward, SmartFire Introduction, pages printed from a website, 3 pages, pp. 1-3, date last visited Jan. 17, 2008, http://www.woodward.com/engine/gaseg/smartfire/smart.cfm.

Heejung Jung et al., Measurement of Electrical Charge on Diesel Particles, article, Oct. 17, 2005, 7 pages, pp. 1129-1135, 39:1129-1135, 2005, Aerosol Science and Technology.

Guenther Hauser, Smoke Particulate Sensors of OBD and High Precision Measuring, paper, Oct. 31-Nov. 2, 2006, 16 pages, 2006-01-3549, SAE Technical Paper Series, Commercial Vehicle Engineering, Congress and Exhibition, Chicago, Illinois; SAE International, 400 Commonwealth Drive, Warrendale, PA 15096-0001 USA.

W.D.E. Allan et al., Development of a Smoke Sensor for Diesel Engines, paper, Oct. 27-30, 2003, 8 pages, 2003-01-3084, SAE Technical Paper Series, Powertrain & Fluid Systems, Conference & Exhibition, Pittsburgh, Pennsylvania USA; SAE International, 400 Commonwealth Drive, Warrendale, PA 15096-0001 USA.

* cited by examiner

SURFACE GAP SOOT SENSOR FOR EXHAUST

FIELD OF THE INVENTION

This invention generally relates to engine exhaust systems and more particularly systems and methods for sensing particulate matter generation within an exhaust system.

BACKGROUND OF THE INVENTION

Increasing environmental restrictions and regulations are causing diesel engine manufacturers and packagers to develop technologies that improve and reduce the impact that operation of such engines have on the environment. As a result, much design work has gone into the controls that operate the combustion process within the engine itself in an attempt to increase fuel economy and reduce emissions such as $NO_x$ and particulate matter (e.g. soot). However, given the operating variables and parameters over which a diesel engine operates and given the tradeoff between $NO_x$ and particulate generation, many engine manufacturers and packagers have found it useful or necessary to apply exhaust after-treatment devices to their systems. These devices are used to filter the exhaust gas flow from the diesel engine to remove or reduce to acceptable levels certain emissions. Such devices are particularly useful in removing exhaust particulates, or soot, from the exhaust gas flow before such soot is released into the environment.

One such exhaust after-treatment device is called a Diesel Particulate Filter (DPF). The DPF is positioned in the exhaust system such that all exhaust gases from the diesel engine flow through it. The DPF is configured so that the particles in the exhaust gas are deposited in the filter substrate of the DPF. In this way, the particulates are filtered out of the exhaust gas so that the engine or engine system can meet or exceed the environmental regulations that apply thereto.

While such devices provide a significant environmental benefit, as with any filter, problems may occur as the DPF continues to accumulate these particulates. After a period of time the DPF becomes sufficiently loaded with soot that the exhaust gases experience a significant pressure drop passing through the increasingly restrictive filter. As a result of operating with an overly restrictive filter, the engine thermal efficiency declines because the engine must work harder and harder simply to pump the exhaust gases through the loaded DPF. Besides the reduced thermal efficiency, a second and potentially more dangerous problem may occur. Because the particulates such as soot accumulated in the DPF are flammable, continued operation with a loaded DPF raises the serious potential for uncontrolled exhaust fires if and when the accumulated soot is eventually ignited and burns uncontrollably.

To avoid either occurrence the engine packager typically incorporates one of several possible filter heating devices upstream of the DPF to periodically clean the filter. These filter heating devices are used periodically to artificially raise the temperature of the exhaust stream to a point at which the accumulated particulates will self-ignite. When initiated at a time before loading of the DPF becomes excessive, the ignition and burn off will occur in a safe and controlled fashion. This process of burning the particulate matter in such a controlled manner is called regeneration. The control of the method to generate the supplemental heat necessary to increase the temperature in the DPF is critical to the safe and reliable regeneration. Typically the acceptable regeneration range is from 600 to 900° C. Temperatures below this range are insufficient to ignite the accumulated particulate matter, and temperatures above this range may cause thermal damage to the filter media.

The rate at which particulates accumulates in the filter depends entirely upon the operating regime of the engine and the engine manufacturer or packager must also determine when to initiate the regeneration process. If regeneration is initiated too soon when the DPF is only lightly loaded, the process will be inefficient. If the regeneration is not initiated until the DPF is heavily loaded, the overall engine efficiency would have been unduly reduced as discussed above and there is a risk that the particulate matter may self-ignite and/or that the burn may be unsafe and uncontrolled.

In an attempt to properly determine when to initiate the regeneration process, several sensors and control algorithms have been developed. These sensors and control algorithms are used to estimate the particulate or soot loading of the DPF so that regeneration can be initiated only after particulate loading could cause an engine efficiency reduction but before excessive loading occurs actually resulting in such an efficiency reduction and raising the potential for self-ignition.

Besides determining when to initiate regeneration of a downstream DPF, monitoring particulate production within an exhaust stream can also provide engine operating feed back to the operator. Particulate matter is typically formed when an engine is running fuel rich, i.e. too much fuel is being injected into the engine such that it cannot be entirely combusted during the combustion cycle. Thus, a high level of particulate production sensed within the exhaust stream can indicate that the engine is running fuel rich and thus wasting fuel or at less than optimum condition.

Several downfalls exist with regard to current particulate sensing technology.

A first disadvantage of current sensors is the level of the signals generated by the sensors. Systems that measure the collection of particle charges on an electrode within the exhaust flow must measure very small amplitude electrical signals within the nano-ampere to micro-ampere range. This low signal level requires extreme amplification and conditioning which is not practical for application on vehicle systems.

A second disadvantage of current sensors relates to maintaining the electrode surface required for signal quality. Resistive heaters, catalyzed surfaces, insulated surfaces and spark cleaning have been used for cleaning of the electrode surfaces or attempting to prevent particulate build-up. These cleaning methods add cost and complexity to the design of the sensor.

A third disadvantage of current sensors relates to requirement of complex algorithms to make use of the electrical signal from the sensor. High speed analysis of spark discharges or small charge transfer often must incorporate compensation for exhaust and engine parameters such as temperature, humidity, fuel type, RPM, etc. This may result in a signal that is not robust and may be easily altered by conditions of the systems or may require exhaustive calibration. Further, this also adds to the increased processing power required to process the information.

BRIEF SUMMARY OF THE INVENTION

In view of the above, embodiments of the present invention provide new and improved systems and methods for sensing particulates, e.g. soot, within an exhaust flow to provide feedback to an operator. This feedback information can be used for a plurality of reasons including. For example, but not limited to, the information can be used to determine particulate loading in a DPF to more effectively initiate a regeneration process to burn off the accumulated particulate in the DPF. Additionally, this information can be used to provide feedback relating to the engine operating conditions. Further yet, the information can be used to determine the condition or health of a DPF.

In one embodiment, a soot sensing arrangement for sensing soot within an exhaust flow is provided. The soot sensing arrangement includes a pair of spaced apart electrodes having an insulator interposed therebetween. These components, when in use, will be positioned in an exhaust flow conduit, e.g., an exhaust manifold or exhaust pipe, such that at least the first electrode, second electrode and insulator extend into the exhaust flow. In this arrangement, the exhaust flow impinges on the first electrode, second electrode and insulator and any soot or particulate therein can likewise impinge thereon. The soot sensing arrangement also includes a voltage supply operably coupled to the first and second electrodes providing a predetermined voltage between the first and second electrodes. Finally, a current sensor operably coupled to the first and second electrodes senses current between the first and second electrodes.

In a preferred embodiment, the soot sensing arrangement further includes a first air gap between the first electrode and the insulator and a second air gap formed between the second electrode and the insulator so as to further isolate the two electrodes and prevent current flow.

Because embodiments of the present invention are aimed at a simplified sensor that does not need complex coatings, some embodiments are have electrodes that are free of any passivation material, such as required in U.S. Pat. Publ. No. 2005/0145023 to Rhodes et al., free of an insulating material formed thereon and/or free of any catalysts thereon.

In preferred embodiments, the first and second electrodes have a potential difference of between about 200 volts and 1000 volts and more preferably between about 400 volts and 600 volts.

A controller arrangement for processing the data sensed by the current sensor may also be provided. In some embodiments, the output of the sensor is a current in the milli-amp range such that the controller arrangement is free of any filtering or conditioning for processing the data generated by the current sensor. This range of amperage puts the sensor in line with other standard sensors used in engine technology.

In a particular implementation, the first electrode is a circular disk, the second electrode is an annular ring, and the insulator is a frusto-conical body interposed between the disk and ring.

In a further embodiment, a method of sensing particulate matter within an exhaust stream at a first location of the exhaust stream of an engine is provided. The sensing uses a first sensor having a first electrode, a second electrode and an insulator that is interposed between and separating the first and second electrodes. The method comprises the steps of providing a potential difference between the first and second electrodes; collecting particulate matter on the surfaces of the first and second electrodes and the insulator to form a plurality of particulate bridges connecting the first and second electrodes; and monitoring a current between the first and second electrodes due to the particulate bridges to form current data.

Further implementations of the method, comprise the step of correlating the current data to particulate data relating to an amount of particulate matter flowing through the exhaust stream.

The method may also include the step of breaking the particulate bridges without the use of a catalyst material or different potential difference between the first and second electrodes. More particularly, when the current passes through the particulate bridges the particulate bridges substantially simultaneous break without the use of a catalyst material or different potential difference due to either repulsion of the particulates from the sensor or burning of particulates such that gaps within the bridge are formed breaking the electrically conductive pathway provided by the particulate bridge. The burning may result do to resistance within the pathway generated by the particulates.

Some methods include integrating the current data to determine an estimated amount of particulate matter that has passed through the exhaust stream. It should be noted that the analysis of the current data can be done with or without directly correlating the current data to soot concentration during analysis data as the two sets of data are effectively the same for a particular system. However, calibration for a given system will be required such as to determine total soot through the exhaust system. This is because depending on the system variable, such as exhaust pipe diameter, engine type, flow rate, etc., the actual amount of soot may vary while actual concentration levels sensed may be the same but sensed in different systems. Again, because the sensed data generally relates to soot/particulate concentration, the total exhaust flow may be required for various calculations relating to the total soot flow. This data may be gathered in many ways such as by a separate sensor in the exhaust flow or from the engine controller output.

Embodiments of the methods may also include initiating a regeneration cycle of a DPF when the estimated amount of particulate matter exceeds a predetermined value.

The method may include the step of comparing the current data to a predetermined threshold value range and adjusting the operation of the engine when the current data is outside of the predetermined threshold value range.

Finally, methods according to embodiments of the present invention may include sensing the particulate matter within the exhaust stream at a two separate locations. One location is upstream of a component within the exhaust stream and a second location being downstream of the component. The method will typically use two identical or similar sensors. The method will include gathering the current data from the two separate sensors and comparing the current data generated by the first sensor with the current data of the second sensor. From this data, the status of the component can be analyzed. The method may include communicating a warning to the operator when the difference between the two sets of current data is outside of a predetermined range.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1:
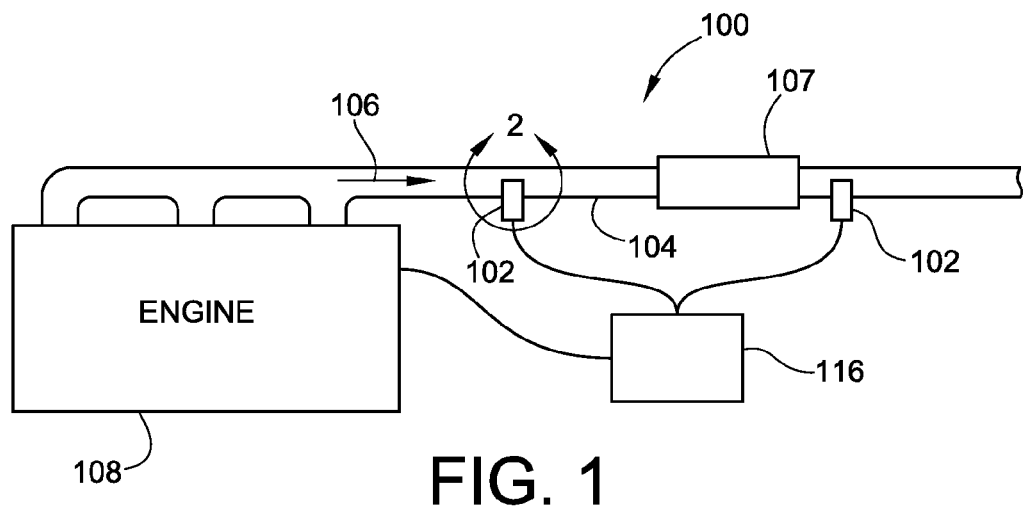
FIG. 1 is a schematic representation of an engine and an exhaust system of the engine including a soot sensor according to an embodiment of the present invention.

FIG. 1 is a simplified schematic representation of an embodiment of a particulate sensor arrangement 100 (also referred to herein as a "soot sensor arrangement 100") according to the teachings of the present invention. As used herein "particulates," "particles," and "soot" are generally synonymous for purposes of understanding the embodiments of the present invention. The soot sensor arrangement 100 includes a sensor 102 mounted within an exhaust pipe 104. Exhaust 106 (illustrated as arrow 106) flowing through the exhaust pipe 104 generated by engine 108 impinges on the sensor 102 and the sensor provides feedback as to the concentration of particulate matter within the exhaust flow 106. While the sensor is illustrated in an exhaust pipe 104, the sensor 102 could be used in other locations along the exhaust flow path, such as within the exhaust manifold, downstream of any boost device or downstream from a DPF 107.

As illustrated in FIG. 1, a plurality of sensors 102 may be used to monitor the particulate matter concentration of the exhaust 106 at various locations to determine, for example, the cleaning efficiency of the DPF 107 by comparing readings both upstream and downstream of the DPF 107.

Figure 2:
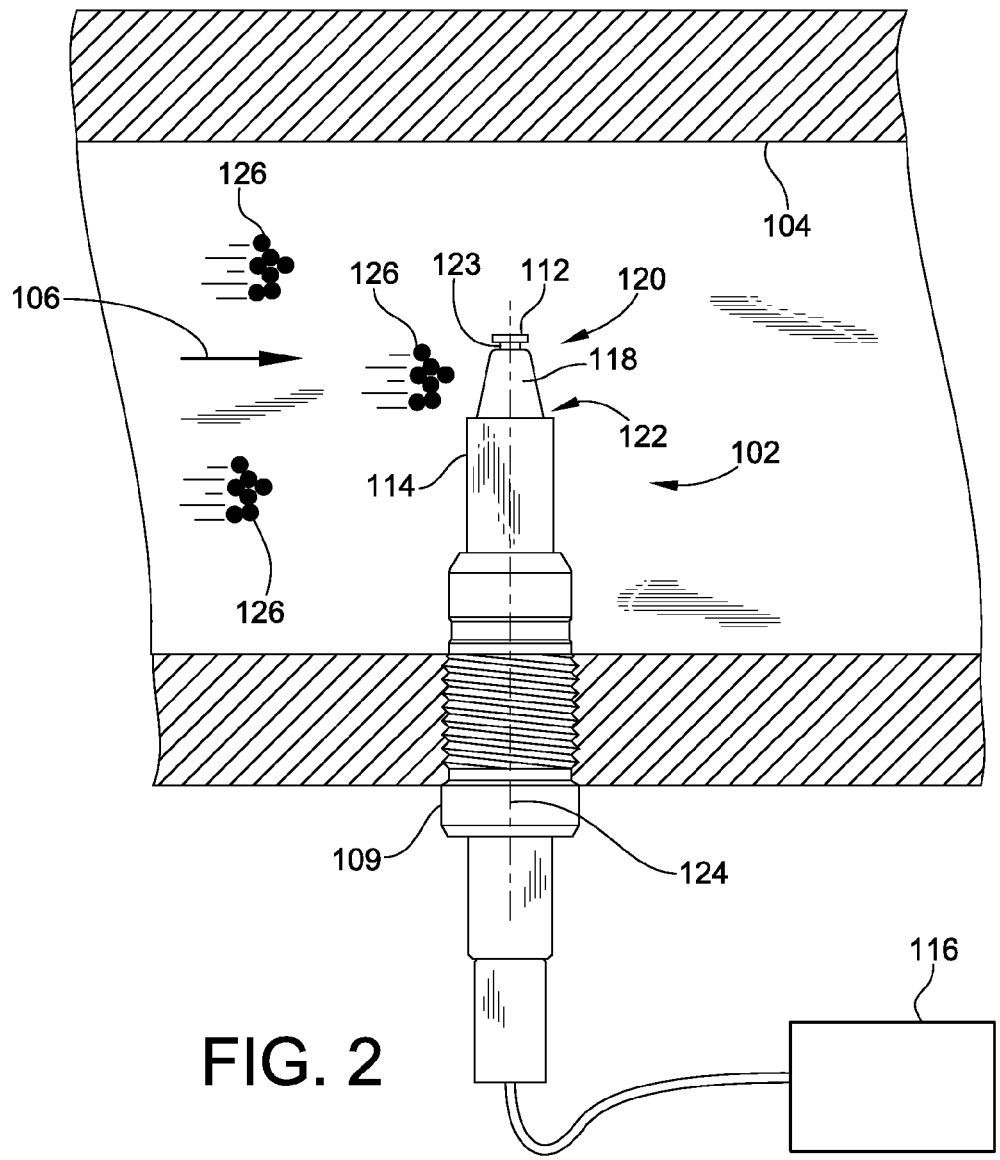
FIG. 2 is an enlarged simplified illustration of the soot sensor of the system of FIG. 1.

FIG. 2 is a simplified illustration of one embodiment of a soot sensor 102 according to the teachings of the present invention. The soot sensor 102 is installed within exhaust flow 106. The soot sensor 102 may include a threaded surface 109 for releasably installing the soot sensor 102 into the flow path such as being threaded into the sidewall or a fitting mounted in the sidewall of the exhaust manifold or exhaust pipe 104.

The soot sensor 102 generally includes charged electrode 112 and ground electrode 114. Controller/processor 116 (illustrated as a single component but could be separate components) includes a voltage supply that provides a DC bias, i.e. potential difference, between the charged electrode 112 and ground electrode 114. Preferably, the DC bias is between about 200 volts and 1000 volts and more preferably between about 400 volts and 600 volts. Notably, the voltage supply could be an independent component and its application to electrodes 112, 114 could merely be controlled by controller/processor 116. In some forms of the invention, the controller/processor 116 may be considered part of the sensor.

Figure 10:
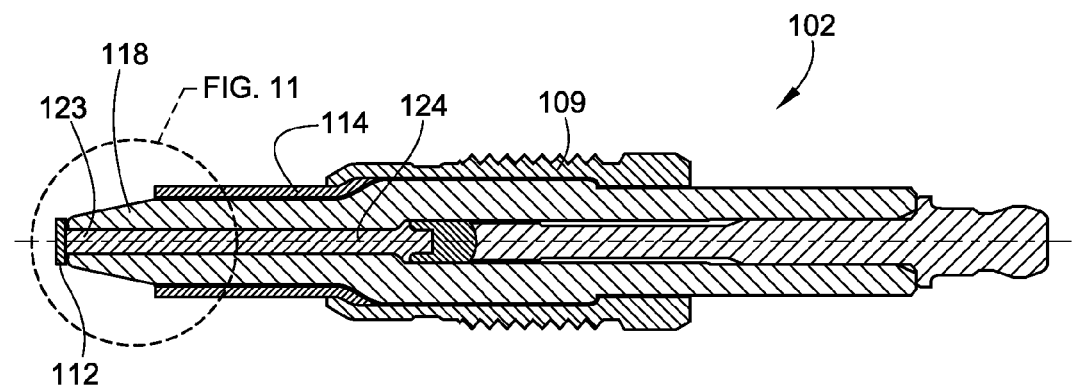
FIGS. 10 and 11 are cross-sectional illustrations of the soot sensor of FIG. 2.
Figure 11:
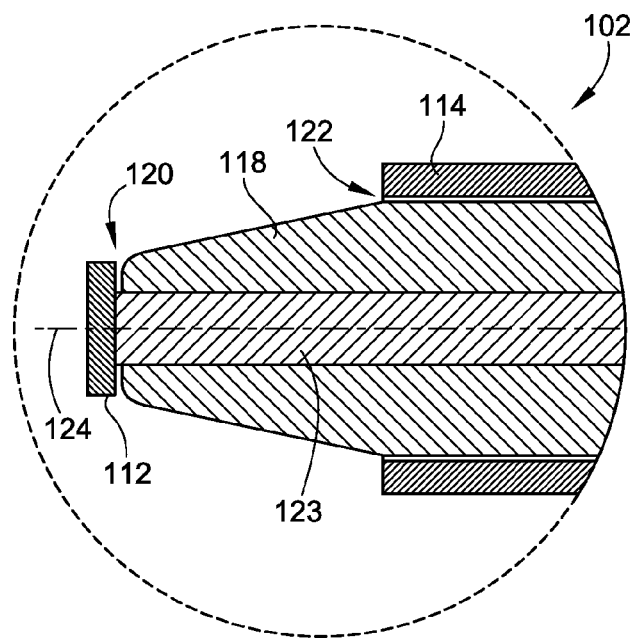

At least a portion of insulator 118 is axially interposed between the charged electrode 112 and ground electrode 114 to inhibit electrical current from flowing between the electrodes in a clean state. With primary reference to FIGS. 10 and 11, to further prevent any significant electrical current from flowing across the electrodes 112, 114, first air gap 120 is formed between the charged electrode 112 and the insulator 118 and second air gap 122 is formed between the ground electrode 114 and the insulator 118. The first air gap 120 is preferably less than 0.3 inches, more preferably less than 0.2 inches, more preferably less than 0.15 inches and even more preferably less than 0.1 inches. The second air gap 122 is preferably less than 0.3 inches, more preferably less than 0.2 inches, more preferably less than 0.15 inches and even more preferably less than 0.1 inches.

Post 123 does extend through air gaps 120 and 122 to operably electrically connect electrode 112 to the controller/processor 116. However, the post 123 is sufficiently inward from the outer surfaces of the electrodes 112, 114 and insulator 118 that it has negligible effects on the operation of the sensor 102.

In the illustrated embodiment, the charged electrode 112 is in the form of a disk and forms the distal end portion of the soot sensor 102. The charged electrode 112 has a diameter of between about 0.2 and 0.5 inches and more preferably a diameter of between about 0.3 and 0.4 inches. The charged electrode 112 has an axial thickness of between about 0.1 and 0.3 inches and more preferably a thickness of between about 0.1 and 0.2 inches. However, other shapes and sizes are contemplated in practicing embodiments of the present invention. These are representative sizes but other sizes are contemplated.

The ground electrode 114 is in the form of a generally annular ring surround part of insulator 118. The ground electrode 114 has an outer diameter of between about 0.3 and 1 inch and more preferably an outer diameter of between about 0.4 and 0.8 inches The annular ring has an inner diameter of between about 0.25 and 0.95 inches and more preferably an inner diameter of between about 0.3 and 0.7 inches. These are representative sizes but other sizes are contemplated.

Further, the electrodes 112, 114 are a metal material formed of standard material for forming spark plug electrodes used for ignition of fuel within an engine. In a preferred embodiment, the electrodes 112, 114 are free of any insulating (e.g. passivating) or catalyzing surfaces as such surfaces will increase cost and are contemplated to inhibit the operation of regeneration processes of the sensor 102.

The insulator 118 in the illustrated embodiment is a generally rotation symmetric structure and has a generally frustoconical end portion due to the charged electrode 112 having a smaller diametrical size than the ground electrode 114. The insulator 118 has a major diameter proximate ground electrode 114 of between about 0.25 and 0.9 inches and a minor diameter proximate charged electrode 112 of between about 0.2 and 0.5 inches. The axial length of the insulator 118 extending between charged electrode 112 and the free end of ground electrode 114 parallel to post 123 and central axis 124 is between about 0.5 and 1 inch. These are representative sizes but other sizes are contemplated.

However, other insulator shapes are contemplated. Preferably, the insulator shape corresponds to the shapes of the electrodes 112, 114. E.g., rounded shapes with rounded electrodes 112, 114 and more rectangular or polygonal shapes when using similar shaped electrodes. The charged electrode 112, ground electrode 114 and insulator 118 are generally coaxial sharing common central axis 124. The soot sensor 102, and particularly electrodes 112, 114 and insulator 118 can be combined into a single module of individual components that are all interconnected such that they can all be removed or installed in the exhaust flow 106 as a single component.

However, other shapes and configurations of the soot sensor are contemplated. For instance, the two electrodes 112, 114 and insulator 118 could all be formed as separate components not coupled together such that they are all substantially discrete pieces. For instance, the two electrodes 112, 114 could be individual plates separately mounted within the exhaust flow. Likewise, the insulator 118 could be separately mounted within the exhaust flow but between the two electrodes 112, 114.

Controller/processor 116 is configured to monitor or sense any current flowing between the charged electrode 112 and ground electrode 114. The controller/processor 116 may also include memory for storing as well as a processor for analyzing the current data that is gathered. Again, it should be noted that the device for sensing or monitoring the current between electrodes 112, 114 could be a separate component that sends a signal to the controller/processor 116.

Figure 3:
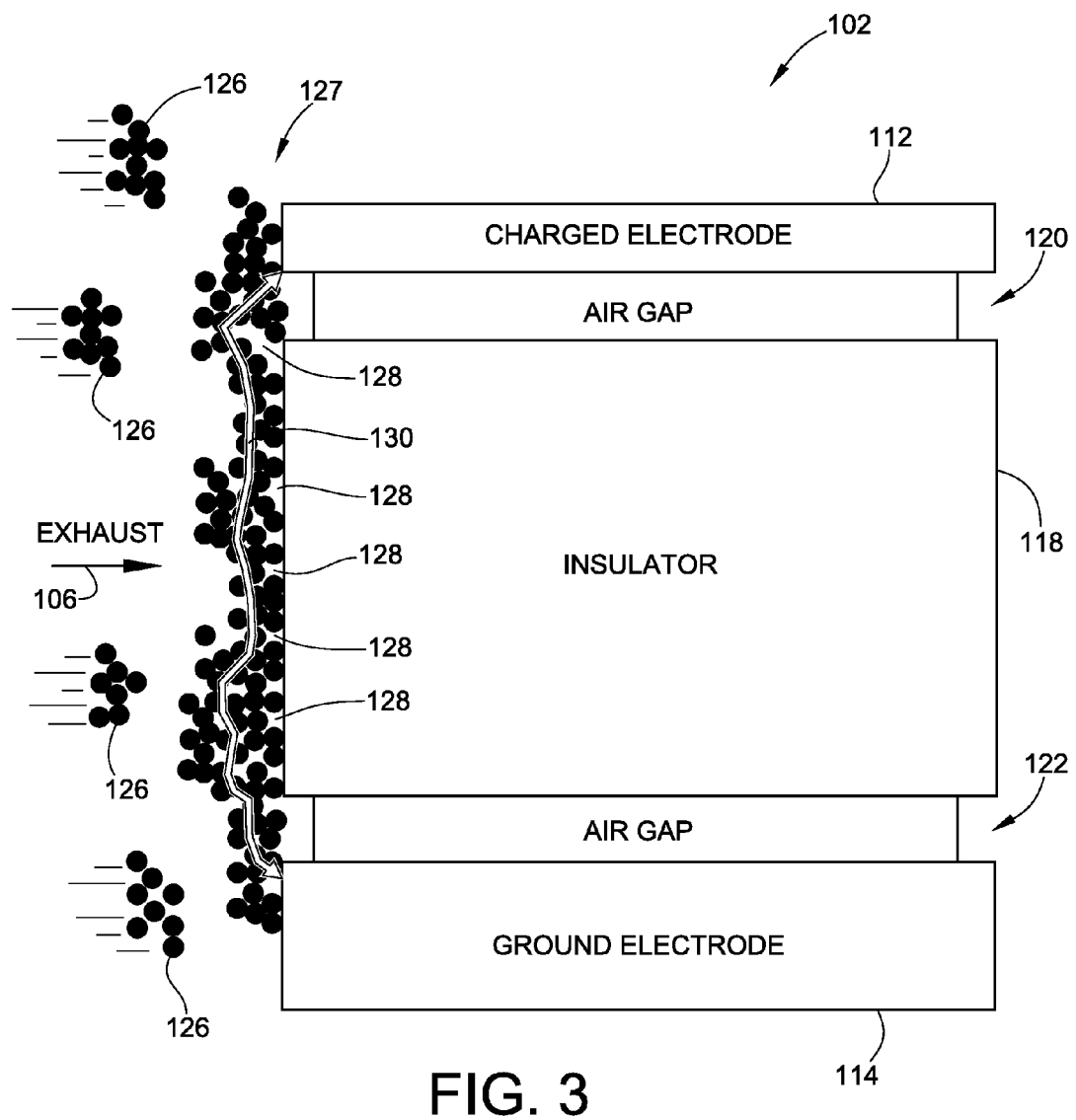
FIG. 3 is an enlarged simplified illustration of the electrode and insulator arrangement of the soot sensor of FIG. 2.

With reference to FIG. 3, an enlarged and simplified schematic of the soot sensor 102, the operation of the soot sensor 102 will be described.

As the individual particulates 126 flow within exhaust 106, the particulates 126 will impinge upon the exposed surfaces of the soot sensor 102. Particulate matter accumulates on the surfaces of the sensor forming a base layer 127 of particulate accumulation.

As the particulate layer 127 begins to accumulate gaps 128 are formed on the soot sensor 102 between individual particulates 126. These gaps 128 are non-conducting gaps 128 and prevent any significant electrical current from flowing between the electrodes. However, as individual particulates 126 continue to impinge on the soot sensor 102, and the layer 127 of particulates that is accumulating thereon, the individual particulates 126 begin to fill the gaps 128 between adjacent particulates.

Because these particulates are at least moderately electrically conductive, once this layer 127 has adequately accumulated and the gaps 128 are filled-in, and first and second air gaps 120, 122 have been bridged, a conductive pathway 130 is formed by the plurality of contacting particulates 126 that permit a flow of electricity, i.e. current, to travel between electrodes 112, 114.

Figure 4:
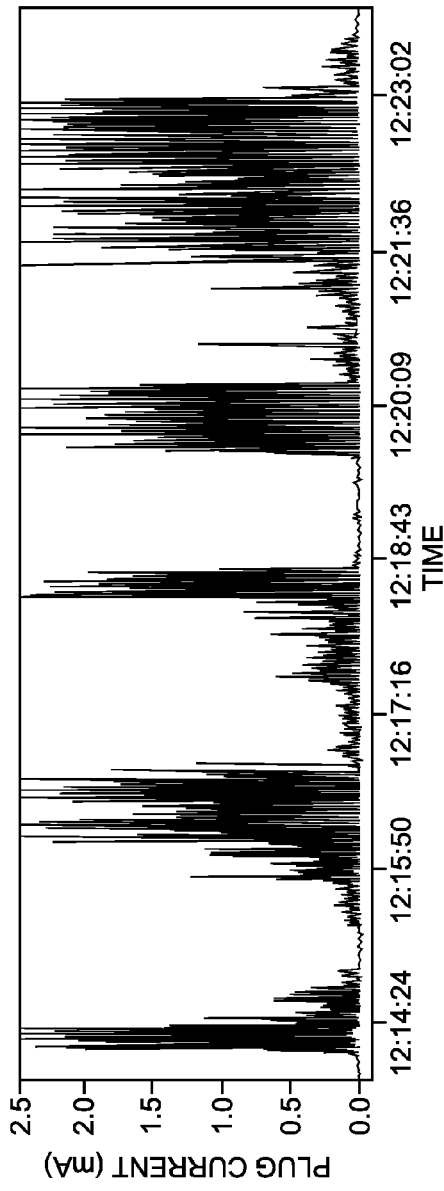
FIG. 4 is a plot of experimental current data acquired during a test of the soot sensor of FIG. 1.

This flow of current can then be monitored or gathered by controller/processor 116 for later analysis. FIG. 4 is a sample plot of current data gathered using an experimental embodiment of a soot sensor 102 according to the present invention. The peaks on the plot illustrate when current was permitted to travel between the electrodes 112, 114. It is notable from FIG. 4 that appreciable current readings well in the milli-amp range are experienced using soot sensor 102. This range is significantly greater than standard soot sensor arrangement as noted previously that typically remain in the nano- or micro-amp ranges. By obtaining current readings well into the milli-amp range, limited to no amplifiers or conditioning of the signal from the soot sensor 102 required for further analysis of the data collected using the soot sensor 102. Further, the soot sensor 102 will provide signal value, more comparable to other standard sensors used in the industry.

In preferred embodiments, the soot sensor senses data having 80, 85, 90, 95 percent of the current data greater than on-tenth of a milli-amp. As such, in preferred embodiments, the controller that processes the current data sensed by the current sensor can be free of any amplification for processing the signal from the current sensor. Preferably, the controller can also be free of any filter or conditioning as well.

The current value will fluctuate depending on the rate that the gaps 128 are being filled by particulates 126. More particularly, when particulate concentration with in the exhaust flow 106 increases, the rate at which particulates impinge on the soot sensor 102 will increase even if exhaust flow rate remains the same. This causes the sensed current flowing between electrodes 112, 114 to increase because the presence of more particulates causes more conductive pathways to be generated reducing resistance between electrodes 112, 114 such that an effectively enlarged conductive pathway 130 is generated.

Further, exhaust flow rate may also affect the rate at which pathways are formed such that this information may also be used to correlate the data sensed from the soot sensor into more useable soot information, such as total soot over a period of time, soot concentration, etc. In other words, there may be a correlation between sensed soot concentration and current flow sensed.

Figure 9:
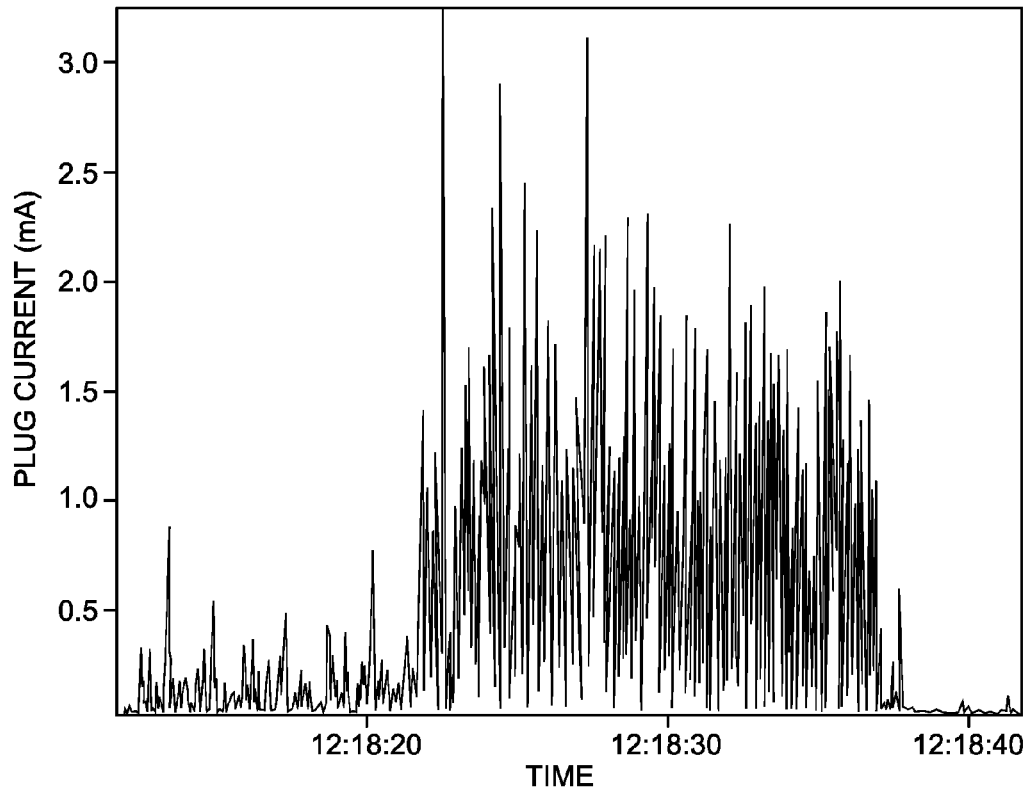
FIG. 9 is an enlarged plot of current data obtained using a soot sensor according to an embodiment of the present invention.

As illustrated in FIG. 4 (and better illustrated in FIG. 9), the current values are individual spikes and current is not continuously increasing as time passes as the cumulative number of particles that impinge on the soot sensor 102 increases. It is believed that there is a regenerative effect that occurs under certain conditions that when the pulses of current pass through the conductive pathway 130 sufficient sparking or heat is generated to burn away or repulse particulates from the soot sensor 102 such that a base line reading, of just above zero mA is observed. Due to this regeneration, the number of pathways 130 does not aggregate such that the sensed current flow does not continually increase in value due to a continued reduction in resistance between electrodes 112, 114. This regeneration is believed to, if not actually clean the sensor 102, at a minimum, generate new gaps 128 within the pathways 130 to break the conductive path therebetween such that, at least, new pathways 130 must be formed to permit a current flow between the electrodes 112, 114.

This regeneration or cleaning effect is also discussed and illustrated below.

Figure 5:
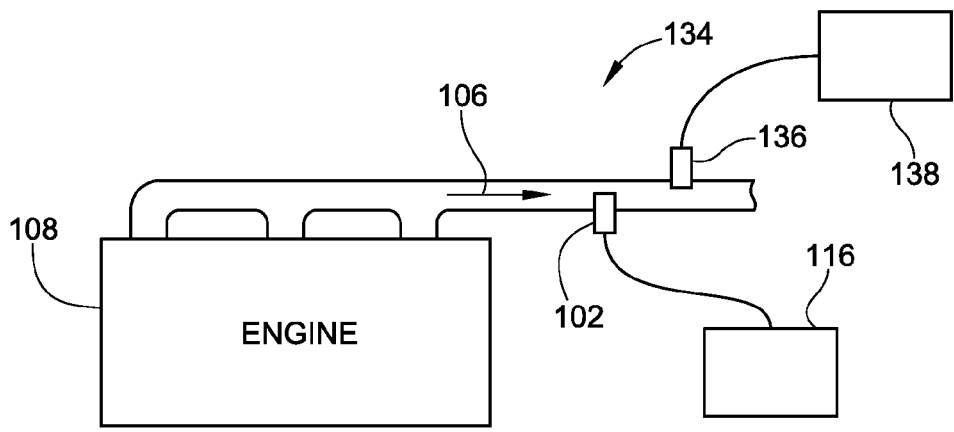
FIG. 5 is an experimental test arrangement similar to the engine and exhaust system of FIG. 1 including a known soot sensor to determine correlation between sensed current and soot concentration.

A test was performed to compare the current readings flowing between the electrodes 112, 114 with a known soot sensor. A schematic representation of the test arrangement 134 is illustrated in FIG. 5. It is substantially similar to FIG. 1 except that there is a known soot sensor 136 slightly downstream from an embodiment of the inventive soot sensor 102. The known soot sensor 136 in the experimental arrangement 134 was an AVL Laser Soot Meter. It was placed approximately one inch from the charged electrode 112.

Figure 6:
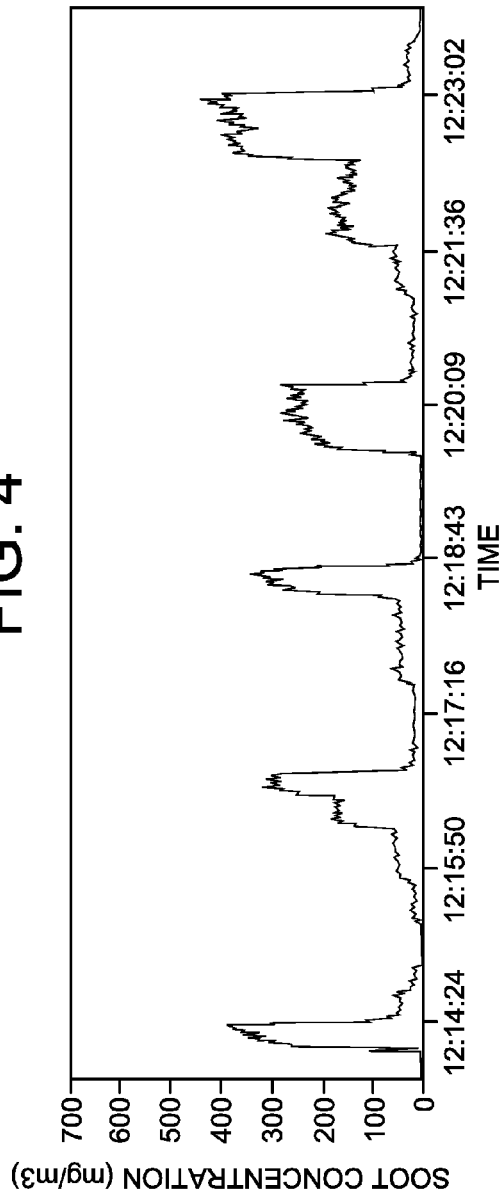
FIG. 6 is the experimental soot concentration data from the known soot sensor in FIG. 5.

The engine 108 was then operated under varying operating conditions to generate various levels, e.g. concentrations, of particulate matter. Over a nine minute period, the output from the known soot sensor 136 and the current data generated by sensor 102 were monitored. The current data from sensor 102 is illustrated in FIG. 4, which plots current (in milli-amps) relative to time. The soot concentration data from the known sensor 136 is illustrated in FIG. 6, which plots soot concentration (in milligrams per meter cubed) relative to time. From these two plots alone, there is illustrated a direct correlation between the sensed current data from sensor 102 and the sensed soot concentration data from known sensor 136, as illustrated by the coordinating peaks and shape in the two separate plots.

Figure 7:
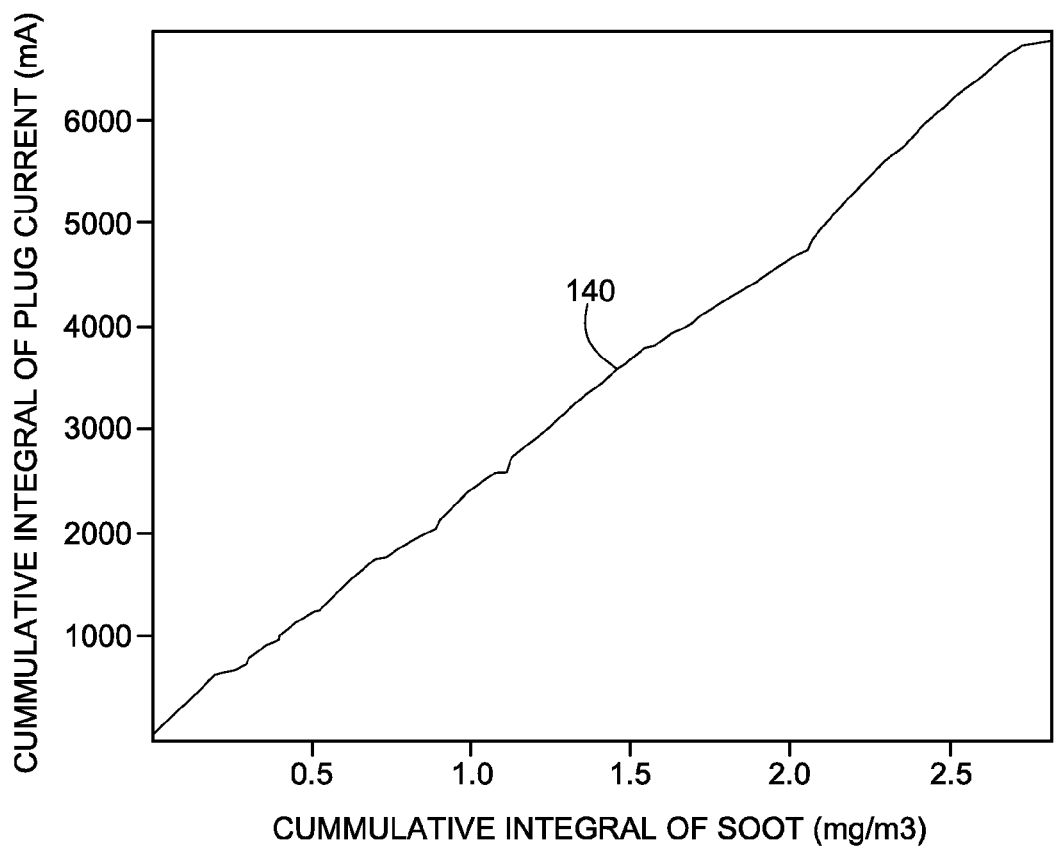
FIG. 7 is a plot of the current data taken from the experimental soot sensor relative to the data taken from the known soot sensor to illustrate the correlation therebetween.

Further, the respective data sets were compared to one another in the plot of FIG. 7. This plot is a plot of the cumulative integral of the current data from sensor 102 plotted relative to the cumulative integral of soot concentration data from known sensor 136. The resulting plot 140 generates a substantially straight line illustrating a strong correlation between the sensed current data from sensor 102 to the particulate concentration of the exhaust flow 106.

As noted above, a regeneration phenomenon of the sensor 102 was also observed. A potential difference of about 500 volts DC was applied across the two electrodes 112, 114. The particular voltage source was limited to a maximum current of 2.5 mA. The response of the sensor 102 was monitored then plotted against time, in FIG. 8. The limit of 2.5 mA is illustrated by the initial flat line value of 2.5 mA in FIG. 8.

Figure 8:
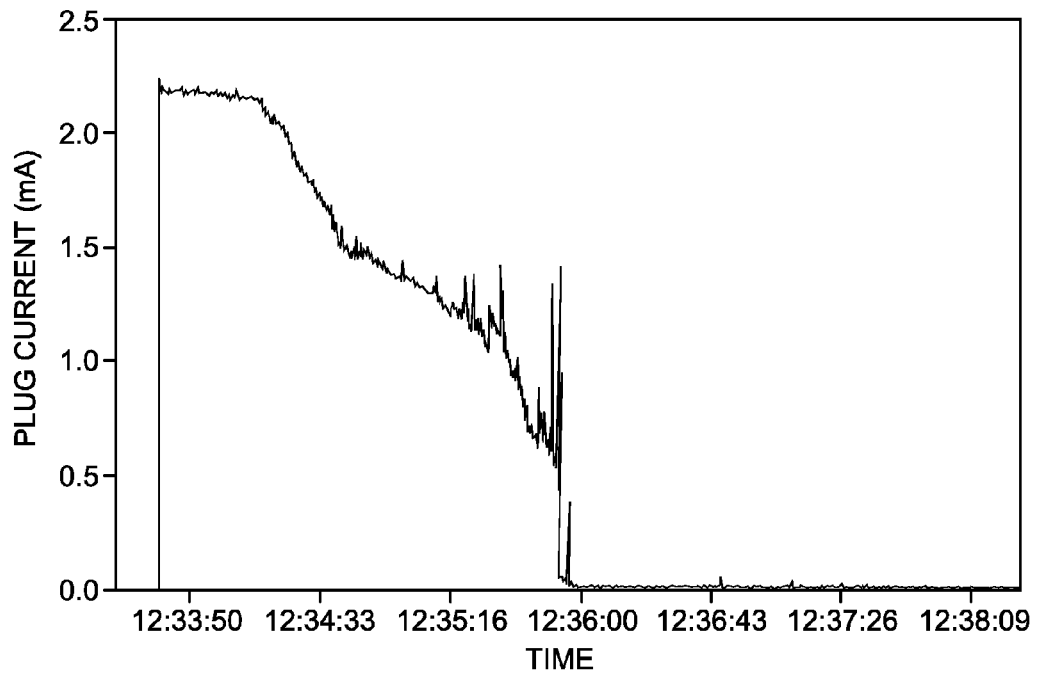
FIG. 8 is a plot illustrating the regenerative effects of the soot sensor of FIG. 1.

It is believed that this regenerative effect occurs when sensor 102 is in exhaust flow 106 and that is why current values of sensor 102 do not continue to increase. At these conditions, a cleaning or regenerative behavior of the soot sensor 102 was observed. It has been observed that once soot particles stop impinging on the soot sensor surfaces, the electrical current begins to decrease and often returns to the levels typical of the base layer 127 only signal. FIG. 8, is a plot illustrating this phenomenon. FIG. 8 plots the response from a heavily loaded soot sensor 102 that was exposed to the electrical conditions identified above, i.e. 500 VDC and maximum current of 2.5 mA, and that after about 3 minutes, the soot sensor 102 returned to a baseline current value of nearly zero mA illustrating that substantially no conductive pathways were present.

It is contemplated that this experienced regeneration is provided due to electrostatic repulsion, breakup of the particulate matter conglomerates through electrical discharge detonation, particle combustion, or other phenomena such that the pathways 130 that permit the electrical current between the electrodes 112, 114 are broken such that new pathways 130 need to be generated. The rate at which these new pathways 130 are generated correlates to the particulate concentration within the exhaust flow.

The information from soot sensor 102 can be used to determine various characteristics of the exhaust system or engine operation based on sensed exhaust soot/particulate concentration. For instance, the controller/processor 116 could do analysis of the feedback from soot sensor 102 to determine that a high rate or concentration of particulates are being generated in the exhaust flow. Thus, the controller/processor 116 can determine that less than optimal operating conditions are being experienced. From that, the engine operating parameters can be altered to adjust the operating conditions of the engine 108. For instance, if too much soot is being generated, this might be the sign that a the engine has gone to a new altitude, such as in an airplane, such that less oxygen is being compressed into the combustion chamber of the engine such that not all fuel is being combusted. Thus, the engine parameter relating to the rate at which fuel is injected into the combustion chamber may be reduced. Alternatively, boost could be increased to increase the amount of oxygen added to the combustion chamber.

The controller/processor 116 could be part of or a separate component than the typical engine controller.

The controller/processor 116 can analyze the current data, such as from FIG. 4, in various ways. For instance, the current data could be correlated to an instantaneous particulate concentration value. Alternatively, as used in FIG. 7, the current data could be integrated to determine a total amount of particulate that has passed through the exhaust system. This aggregate or integrated value can then be used to determine whether a DPF regeneration is necessary if the value is greater than a predetermined value.

Further yet, if multiple current data sets are taken at different locations such as both upstream and downstream of the DPF, these data sets can be used to determine the health or condition of the DPF. More particularly, they can determine if either too much particulate is passing through the DPF and there is damage thereto or alternatively if less than an expected amount of particulates are passing through the DPF such that the DPF may be plugged. Thus, if a difference between the two sets of data is outside of a predetermined range, which may either be greater than or less than a value or within a set range, health and/or operation of the DPF can be determined. Either way, the operator could be warned of the less than desired operating condition of the DPF such that some sort of maintenance or further investigation is required.

Further yet, the controller/processor could create an averaged or approximated current profile, which would correlate to soot concentration, and utilize the slope or rate of change of such a plot to determine various conditions. For instance, if the rate of change of the plot is large, there may have been an upstream change in the system. For instance, the engine operating parameters could have changed. If downstream from a DPF, the DPF could have experienced a failure. This average/ or approximated current profile would look more like the sensor signal in FIG. 6 from the AVL meter. This may be done by using a low pass filter or utilizing running averages. Further analysis may analyze specific frequencies or frequency analysis on the collected data.

Additionally, this sensed data only relates to the rate at which particles form pathways between the two electrodes. Thus, this data may also be combined with additional operating data such as exhaust flow rate to determine additional information such as soot generation over a period of time. This could then be used to determine when to initiate maintenance or regeneration of the DPF.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A soot sensing arrangement or sensing soot within an exhaust flow, the soot sensing arrangement comprising:
   a first electrode;
   a second electrode spaced apart from the first electrode;
   an insulator interposed between the first electrode and second electrode;
   a voltage supply operably coupled to the first and second electrodes providing a predetermined voltage between the first and second electrodes;
   a current sensor operably coupled to the first and second electrodes to sense current between the first and second electrodes; and
   a first air gap between the first electrode and the insulator and a second air gap formed between the second electrode and the insulator;
   wherein the first electrode is a circular disk and the second electrode is an annular ring surrounding part of the insulator, the insulator is a cylindrical insulator having a frusto-conical end portion interposed between the disk and ring.

2. The soot sensing arrangement of claim 1, wherein the first and second electrodes are free of any passivation material.

3. The soot sensing arrangement of claim 1, wherein the first and second electrodes are metal and are free of an insulating material formed thereon.

4. The soot sensing arrangement of claim 1, wherein the first air gap is less than 0.1 inches and the second air gap is less than 0.1 inches.

5. The soot sensing arrangement of claim 2, wherein the first and second electrodes have a potential difference of between about 200 volts and 1000 volts.

6. The soot sensing arrangement of claim 5, wherein the first and second electrodes have a potential difference of between about 400 volts and 600 volts.

7. The soot sensing arrangement of claim 1, further comprising a controller arrangement for processing the data sensed by the current sensor, wherein the controller arrangement is free of any amplification for processing the signal by the current sensor.

8. The soot sensing arrangement of claim 1, further comprising a controller arrangement for processing the data sensed by the current sensor, wherein the controller arrangement is free of any filtering or conditioning for processing the data generated by the current sensor.

9. The soot sensing arrangement of claim 8, wherein the current sensor senses current values within an accuracy of one-tenth of a milli-amp.

10. The soot sensing arrangement of claim 8, wherein the current sensor senses greater than 80% of its current values of a value greater than 0.1 milli-amps.

11. The soot sensing arrangement of claim 1, further including an exhaust flow conduit, wherein the a first electrode, second electrode and insulator extend into the exhaust flow flowing through the exhaust flow conduit such that the exhaust flow impinges on the first electrode, second electrode and insulator.

12. A soot sensing arrangement for ,sensing soot within an exhaust flow, the soot sensing arrangement comprising;
   a first electrode;
   a second electrode spaced apart from the first electrode;
   an insulator interposed between the first electrode and second electrode;
   a voltage supply operably coupled to the first and second electrodes providing a edetermined voltage between the first nd second electrodes;
   a current sensor operably coupled to the first and second electrodes to sense current between the first and second electrodes;
   a first air gap between the first electrode and the insulator and a second air gap formed between the second electrode and the insulator; and
   an exhaust flow conduit, wherein the a first electrode, second electrode and insulator entend into the exhaust flow flowing throuch the exhaust flow conduit such that the exhaust flow impinges on the first electrode, second electrode and insulator;
   wherein the first electrode is a circular disk and the second electrode is an annular ring surrounding part of the insulator, the insulator is a cylindrical insulator having a frusto-conical end portion interposed between the disk and ring.

13. A method of sensing particulate matter within an exhaust stream at a first location of the exhaust stream of an engine using a first sensor having a first electrode, a second electrode and an insulator that is interposed between and separating the first and second electrodes, the method comprising the steps of:
   providing a potential difference between the first and second electrodes,
   wherein the first electrode is a circular disk and the second electrode is an annular ring surrounding part of the insulator, and wherein in the insulator is cylindrical with a frusto-conical end portion interposed between the circular disk and the annular ring;
   collecting particulate matter on the surfaces of the first and second electrodes and the insulator to form a plurality of particulate bridges connecting the first and second electrodes;
   monitoring a current between the first and second electrodes due to the particulate bridges to form current data; and
   breaking the particulate bridges without the use of a catalyst material or different change in potential difference between the first and second electrodes.

14. The method of claim 13, further comprising the step of correlating the current data to particulate data relating to an amount of particulate matter flowing through the exhaust stream.

15. The method of claim 13, further comprising the step of passing the current through the particulate bridges and wherein the step of passing the current through the particulate bridges simultaneously performs the step of breaking the particulate bridges without the use of a catalyst material or changes in potential difference between the first and second electrodes.

16. The method of claim 15, wherein the step of breaking the particulate bridges includes removing portions of the particulate bridges from the particulate bridges.

17. The method of claim 16, wherein the removal of the portions of the particulate bridges is performed by burning of portions of the bridge due to the current that is passed therethrough.

18. The method of claim 13, further comprising using the current data with exhaust flow rate data to determine an estimated amount of particulate matter that has passed through the exhaust stream.

19. The method of claim 18, further comprising the step of initiating a regeneration cycle of a DPF when the estimated amount of particulate matter exceeds a predetermined value.

20. The method of claim 13, further comprising the step of comparing the current data to a predetermined threshold value range and adjusting the operation of the engine when the current data is outside of the predetermined threshold value range.

21. A method of sensing particulate matter within an exhaust stream at a first location of the exhaust stream of an engine using a first sensor having a first electrode, a second electrode and an insulator that is interposed between and separating the first and second electrodes, the method comprising the steps of:

providing a potential difference between the first and electrodes, wherein the first electrode is a circular disk and the second electrode is an annular ring surrounding part of the insulator, and wherein in the insulator is cylindrical with a frusto-conical end portion interposed between the circular disk and the annular ring;

collecting particulate matter on the surfaces of the first and second electrodes and the insulator to form a plurality of particulate bridges connecting the first and second electrodes;

monitoring a current between the first and second electrodes due to the particulate bridges to form current data; and further comprising sensing the particulate matter within the exhaust stream at a second location, the first location being upstream of a component within the exhaust stream and the second location being downstream of the component, using a second sensor similar to the first sensor, but located at the second location, further comprising comparing the current data generated by the first sensor with the current data of the second sensor and further comprising communicating a warning to the operator when the difference between the two sets of current data is outside of a predetermined range.

* * * * *

UNITED STATES PATENT AND TRADEMARK OFFICE
CERTIFICATE OF CORRECTION

PATENT NO. : 8,310,249 B2  
APPLICATION NO. : 12/561666  
DATED : November 13, 2012  
INVENTOR(S) : Clark Paterson Page 1 of 1

It is certified that error appears in the above-identified patent and that said Letters Patent is hereby corrected as shown below:

Claim 12
Column 11, Line 1, after "arrangement for" delete ",".

Column 12, Line 8, "edetermined" should be changed to --predetermined--.

Column 12, Line 9, "nd" should be changed to --and--.

Signed and Sealed this
Nineteenth Day of February, 2013

Teresa Stanek Rea
*Acting Director of the United States Patent and Trademark Office*